US010368726B2

(12) United States Patent
Perez-Lizano

(10) Patent No.: US 10,368,726 B2
(45) Date of Patent: Aug. 6, 2019

(54) INTUBATION DEVICE CAPABLE OF BI-DIRECTIONAL DISTAL DEFLECTION AND TEMPORARY PROXIMAL, SHAPING FOR LARYNGOSCOPY, TRACHEOSCOPY, AND BRONCHOSCOPY

(71) Applicant: Edward R. Perez-Lizano, San Diego, CA (US)

(72) Inventor: Edward R. Perez-Lizano, San Diego, CA (US)

( * ) Notice: Subject to any disclaimer, the term of this patent is extended or adjusted under 35 U.S.C. 154(b) by 199 days.

(21) Appl. No.: 14/773,735

(22) PCT Filed: Mar. 14, 2014

(86) PCT No.: PCT/US2014/028737
§ 371 (c)(1),
(2) Date: Sep. 8, 2015

(87) PCT Pub. No.: WO2014/200593
PCT Pub. Date: Dec. 18, 2014

(65) Prior Publication Data
US 2016/0038001 A1 Feb. 11, 2016

Related U.S. Application Data

(60) Provisional application No. 61/883,885, filed on Sep. 27, 2013, provisional application No. 61/794,566, filed on Mar. 15, 2013.

(51) Int. Cl.
*A61B 1/005* (2006.01)
*A61M 16/04* (2006.01)
(Continued)

(52) U.S. Cl.
CPC .......... *A61B 1/0051* (2013.01); *A61B 1/0052* (2013.01); *A61B 1/00073* (2013.01);
(Continued)

(58) Field of Classification Search
CPC . A61B 1/0051; A61B 1/00073; A61B 1/0676; A61B 1/05; A61B 1/0052;
(Continued)

(56) References Cited

U.S. PATENT DOCUMENTS 4,746,043 A   5/1988  Booker
5,259,377 A * 11/1993  Schroeder ......... A61M 16/0488
                                                        128/200.24
(Continued)

FOREIGN PATENT DOCUMENTS

DE      195 24 534 C1    6/1996
EP       0 778 044 A2    6/1997
WO    WO 2011/065963 A1  6/2011

OTHER PUBLICATIONS

Supplementary European Search Report dated Oct. 24, 2016, regarding EP 14 81 0570.

*Primary Examiner* — John P Leubecker
*Assistant Examiner* — Genja M Frankert
(74) *Attorney, Agent, or Firm* — DLA Piper LLP (US)

(57) ABSTRACT

The present invention provides a device and system which combines a stylet with imaging and display capabilities to enable visualization of confined spaces.

13 Claims, 12 Drawing Sheets

(51) Int. Cl.
*A61B 1/06* (2006.01)
*A61B 1/267* (2006.01)
*A61B 1/05* (2006.01)
*A61B 1/00* (2006.01)

(52) U.S. Cl.
CPC .............. *A61B 1/05* (2013.01); *A61B 1/0676* (2013.01); *A61B 1/267* (2013.01); *A61M 16/0418* (2014.02); *A61M 16/0488* (2013.01); *A61B 1/00016* (2013.01); *A61B 1/00018* (2013.01); *A61M 2205/3306* (2013.01); *A61M 2205/3569* (2013.01); *A61M 2205/3592* (2013.01); *A61M 2205/502* (2013.01); *A61M 2205/587* (2013.01); *A61M 2205/8206* (2013.01); *A61M 2209/06* (2013.01)

(58) Field of Classification Search
CPC . A61B 1/267; A61B 1/00016; A61B 1/00018; A61M 16/0418; A61M 16/0488; A61M 2205/502; A61M 2205/3592; A61M 2205/3569; A61M 2205/3306; A61M 2209/06; A61M 2205/8206
See application file for complete search history.

(56) References Cited

U.S. PATENT DOCUMENTS

| | | | |
|---|---|---|---|
| 5,454,185 A | 10/1995 | Love | |
| 5,873,842 A | 2/1999 | Brennen | |
| 6,132,390 A | 10/2000 | Cookston et al. | |
| 6,251,080 B1 | 6/2001 | Henkin | |
| 6,379,310 B1 | 4/2002 | Mori | |
| D487,844 S | 3/2004 | Nichols | |
| D496,155 S | 9/2004 | Londono | |
| 6,823,285 B1 | 11/2004 | Bartsch | |
| 7,658,708 B2 | 2/2010 | Schwartz | |
| 7,794,405 B2 | 9/2010 | Karo | |
| 8,114,026 B2 | 2/2012 | Leschinsky | |
| 8,416,291 B2 | 4/2013 | Carrey et al. | |
| 8,534,933 B2 | 9/2013 | Sherwood | |
| 8,652,033 B2 | 2/2014 | Berci | |
| 8,659,421 B2 | 2/2014 | Babineau | |
| D701,504 S | 3/2014 | Christopher | |
| 8,827,899 B2 | 9/2014 | Farr et al. | |
| 9,131,859 B2 | 9/2015 | Sawanoi | |
| 2005/0182297 A1* | 8/2005 | Gravenstein | A61B 1/0017 600/139 |
| 2007/0035042 A1 | 2/2007 | Sakal et al. | |
| 2007/0074720 A1 | 4/2007 | Schwartz | |
| 2007/0106208 A1* | 5/2007 | Uber, III | A61M 5/142 604/65 |
| 2007/0287961 A1* | 12/2007 | Parker | A61B 17/320016 604/164.01 |
| 2008/0236575 A1 | 10/2008 | Chuda | |
| 2008/0312507 A1* | 12/2008 | Kim | A61B 1/00052 600/188 |
| 2009/0322867 A1 | 12/2009 | Carrey et al. | |
| 2010/0108060 A1 | 5/2010 | Pecherer et al. | |
| 2011/0028790 A1* | 2/2011 | Farr | A61B 1/00052 600/187 |
| 2011/0120458 A1* | 5/2011 | Schwartz | A61B 1/267 128/200.26 |
| 2011/0160537 A1 | 6/2011 | Chen | |
| 2011/0207999 A1 | 8/2011 | Torisawa et al. | |
| 2012/0078055 A1 | 3/2012 | Berci | |

* cited by examiner

INTUBATION DEVICE CAPABLE OF BI-DIRECTIONAL DISTAL DEFLECTION AND TEMPORARY PROXIMAL, SHAPING FOR LARYNGOSCOPY, TRACHEOSCOPY, AND BRONCHOSCOPY

CROSS-REFERENCE TO RELATED APPLICATION

This application is a 35 USC § 371 National Stage application of International Application No. PCT/US2014/028737 filed Mar. 14, 2014, now pending; which claims the benefit under 35 USC § 119(e) to U.S. Application Ser. No. 61/883,885 filed Sep. 27, 2013 and to U.S. Application Ser. No. 61/794,566 filed Mar. 15, 2013. The disclosure of each of the prior applications is considered part of and is incorporated by reference in the disclosure of this application.

FIELD OF THE INVENTION

The disclosure relates to imaging devices, and more particularly to devices having an improved functionality for insertion and imaging of an enclosed space, such as a patient's respiratory tract.

BACKGROUND

A wide variety of devices are described in the art that facilitate viewing of confined spaces. Frequently, such devices rely upon fiber optic conduits to transfer the image from the distal end of the fiber optic conduit inserted into the confined space to the operator at the proximal end of the fiber optic conduit. Such confined spaces frequently lack illumination and consequently such viewing systems often provide an illumination source. Examples of such commercially available fiber optic viewing devices include bore scopes, endoscopes, and the like. However, such devices are frequently complex involving a viewing system integral with the fiber-optic channel. Due to the complexity of these devices and the specialized nature of their applications, they are often very expensive restricting their use to professionals whose work demands the use of such instrumentation.

A common procedure that may utilize fiber optic viewing system is endotracheal intubation which is a common technique that is used when an individual must be ventilated such as after receiving a general anesthetic. The technique consists of placing an endotracheal tube (i.e. a flexible, plastic tube) into the patient's trachea to ventilate his/her lungs. During intubation, the endotracheal tube must be inserted past the patient's teeth and tongue and then past the epiglottis and the vocal cords into the trachea.

Devices have been developed that utilize flexible fiberoptics, either alone or in conjunction with endotracheal tubes, to perform intubation. However, such scopes are awkward to use due to the types of displays used along with scopes that are generally non-adjustable and inflexible. Additionally such devices are very costly which limits access to these devices. As such, there is a need for a system that allows illumination and viewing of the respiratory tract during intubation which is also flexible and easily adjustable to ensure ease of intubation.

SUMMARY OF THE INVENTION

The present invention provides a device and system which combines a stylet with imaging and display capabilities to enable visualization of confined spaces. Accordingly, in one aspect, the invention provides an imaging system. The imaging system includes: a) a stylet having a distal end, a proximal end and a deflectable section disposed therebetween; and b) an image acquisition element disposed toward the distal end of the stylet. The stylet includes: i) a first shaft having a distal end and a proximal end, the proximal end of the first shaft being coupled to a first pressure receiving element at the proximal end of the stylet; and ii) a second shaft having a distal end and a proximal end, the distal end of the second shaft being coupled to the distal end of the first shaft at the distal end of the stylet, and the proximal end of the second shaft being coupled to a second pressure receiving element disposed distal to the first pressure receiving element at the proximal end of the stylet, the second pressure receiving element slidably coupled to the first shaft, wherein application of opposing forces to the first and second pressure receiving elements produces a deflection in the deflectable section. In various embodiments, the imaging system further includes an image conduit coupled to the image acquisition element and traversing along the length of the first or second shaft and optionally includes a coupling for operably engaging a display of the system. In another embodiment, the image acquisition element is in wireless communication with the display. In various embodiments, the system further includes a malleable rod removably disposed within a lumen or recess of the first or second shaft.

In another aspect, the invention provides an intubation device. The intubation device includes: a) a stylet having a distal end, a proximal end and a deflectable section disposed therebetween; and b) a malleable rod removably disposed within a lumen or recess of the stylet extending along its length. The stylet further includes: i) a first shaft having a distal end and a proximal end, the proximal end of the first shaft being coupled to a first pressure receiving element at the proximal end of the stylet; and ii) a second shaft having a distal end and a proximal end, the distal end of the second shaft being coupled to the distal end of the first shaft at the distal end of the stylet, and the proximal end of the second shaft being coupled to a second pressure receiving element disposed distal to the first pressure receiving element at the proximal end of the stylet, the second pressure receiving element slidably coupled to the first shaft, wherein application of opposing forces to the first and second pressure receiving elements produces a deflection in the deflectable section. In various embodiments the intubation device further includes an illumination source disposed toward the distal end of the stylet which may be arranged as an array.

In another aspect, the invention provides an imaging system having: a) a stylet having a distal end and a proximal end; b) an image acquisition element disposed toward the distal end of the stylet; and c) a malleable rod removably disposed within a lumen or recess extending along the length of the stylet. The stylet further includes: i) a first shaft having a distal end and a proximal end; and ii) a second shaft having a distal end and a proximal end, the distal end of the second shaft being coupled to the distal end of the first shaft at the distal end of the stylet, and wherein the first shaft and the second shaft are of different lengths. In various embodiments, the imaging system further includes an image conduit coupled to the image acquisition element and traversing along the length of the first or second shaft and optionally includes a coupling for operably engaging a display of the system. In another embodiment, the image acquisition element is in wireless communication with the display. In various embodiments, the system further includes a malleable rod removably disposed within a lumen or recess of the first or second shaft.

In another aspect, the invention provides a kit. The kit may include an imaging system or intubation device as described herein. The kit may further include instructions for obtaining images of a confined space, such as an airway. In some embodiments, the kit further includes one or more spacer elements.

In another aspect, the invention provides a method of intubating a subject. The method includes: a) inserting the stylet of the system of claim 1 into an endotracheal tube; b) insert the stylet and the endotracheal tube into the airway of the subject; c) visualizing the airway of the subject via the image acquisition element; d) inserting the stylet and the endotracheal tube into the trachea of the subject; and e) removing the stylet from the subject's trachea, thereby intubating the subject. In embodiments, the method may further include confirming correct depth of placement of the endotracheal tube in the trachea of the subject. Additionally, a malleable rod may be inserted into the first or second shaft of the stylet and bent to a desired curvature before inserting the stylet in to the airway.

In yet another aspect, the invention provides a method of imaging a confined space. The method includes applying opposing forces to the first and second pressure receiving pads to generate a deflection in the stylet of the present invention, inserting the stylet into the confined space, and visualizing the space via an image acquisition element before, during or after insertion of the device into the confined space, thereby imaging the confined space.

BRIEF DESCRIPTION OF THE FIGURES

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION

Figure 1:
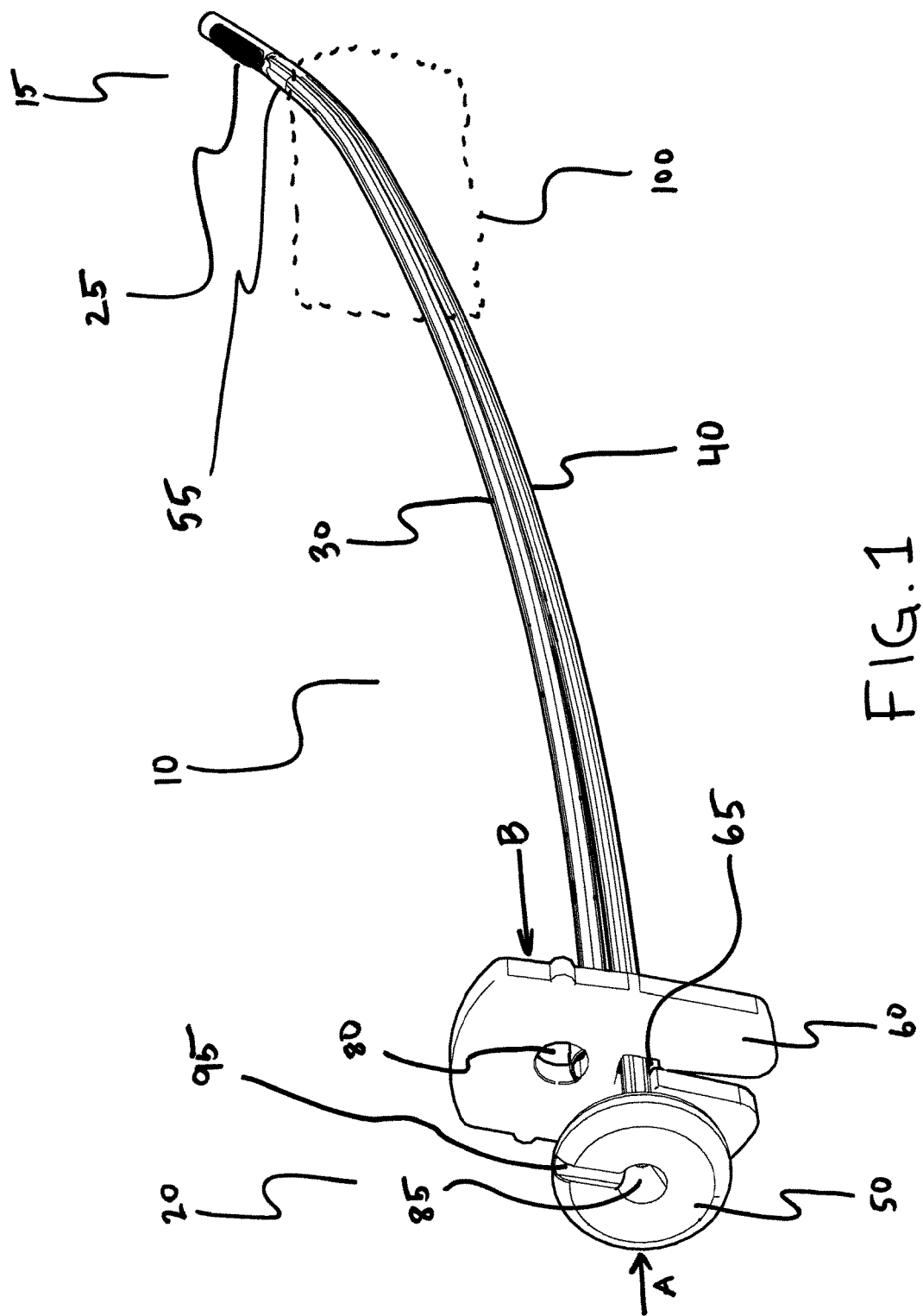
FIG. 1 is a perspective view of one embodiment of a stylet of the disclosure.

The invention relates to an imaging system having improved functionality for imaging of an enclosed space, such as a patient's respiratory tract. As such, the invention provides a device and system which combines a stylet with imaging and display capabilities to enable visualization of confined spaces. The system provides a low cost alternative that exhibits improved functionality as compared to existing imaging systems and is useful in a variety of fields including, but not limited to, medical treatment and diagnosis, surveillance, and mechanical and automotive applications.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

With reference to FIGS. 1-10, the present disclosure generally relates to a system and device for imaging a confined space, such as an airway of a subject. With specific reference to FIGS. 1-3, in general terms, in one embodiment the imaging system includes: a) a stylet (10) having a distal end (15), a proximal end (20) and a deflectable section (100) disposed therebetween; and b) an image acquisition element (25) disposed toward the distal end of the stylet. The stylet includes: i) a first shaft (40) and a second shaft (30). The proximal end of the first shaft is coupled to a first pressure receiving element (50) at the proximal end of the stylet. The distal end of second shaft is coupled to the distal end of the first shaft at the distal end of the stylet (at 55), while the proximal end of the second shaft is coupled to a second pressure receiving element (60) disposed distal to the first pressure receiving element at the proximal end of the stylet. In general, the second pressure receiving element engages the first shaft (i.e., at 65), such that application of opposing forces (arrows A and B) to the first and second pressure receiving elements (50, 60) produces a deflection in the deflectable section (100). As such, application of opposing forces allows deflection of the tip to be adjusted while entering a confined space, such as an airway.

As used herein, the term "image acquisition element" is used to refer to a means to acquire an optical image and convert said optical image into an electronic signal. An image acquisition element may be used to digitize individual still images or for digitization of multiple images in the form of motion picture images. Examples of digital image sensors include the charge coupled device (CCD) or the complementary metal-oxide-semiconductor (CMOS) active pixel sensor imagers. An active pixel sensor imager refers to a two-dimensional array of individual active pixel sensors, each active pixel sensor containing a photo-detector and an active amplifier. Such image acquisition elements are well known in the art as well as others which may be utilized. In one embodiment, the image sensor is a CMOS active pixel sensor imager. CMOS active pixel sensor arrays possess desirable characteristics such as ease of manufacture, low power consumption, and are less prone to the blooming effect where the light source overloads the sensitivity of each individual sensor causing bleeding of the light source into surrounding pixels enabling the use of a brighter light source to assist in visualization. The term image acquisition element may also refer to a component of an infrared thermal scanning system comprising an infrared imaging sensor. Commercially available CCD image sensors are sensitive to near-infrared light which facilitates infrared image capture sufficient for video transmission in zero lux (or near zero lux).

As will be understood by those in the art, the system of the present disclosure may include one or more image acquisition elements, for example 1, 2, 3, 4, 5, 6, 7, 8, 9, 10 or more. Additionally, while at least one image acquisition element is generally disposed toward or at the distal tip of the stylet, an image acquisition element may be located at any point along the length of the stylet to assist in imaging the interior of a cavity. Additionally, an image acquisition element may be angled with respect to the longitudinal axis of the device. In one embodiment, at least one image acquisition element is arranged such that images distal to the distal tip are obtained while any additional image acquisition elements are arranged such that images radial to the longitudinal axis of the stylet may be obtained.

Figure 4:
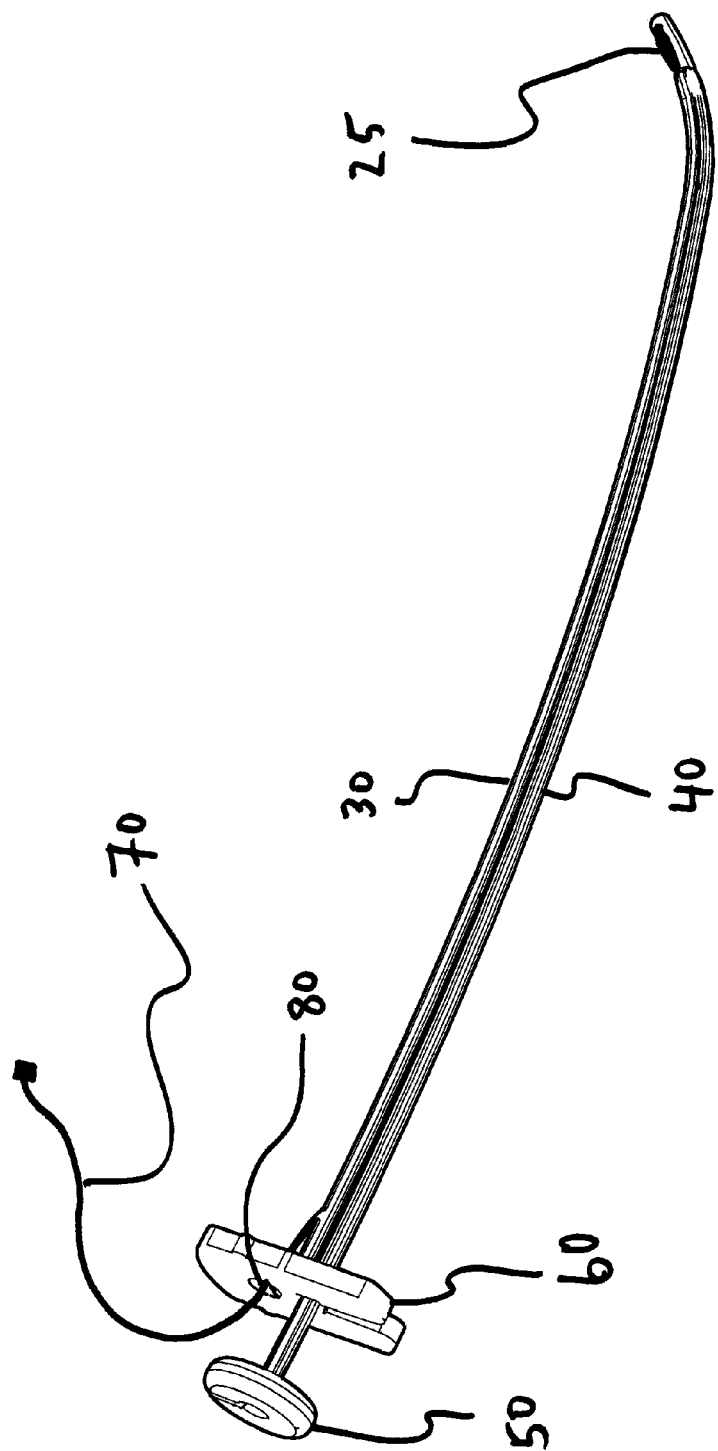
FIG. 4 is a perspective view of one embodiment of a stylet of the disclosure.
Figure 5:
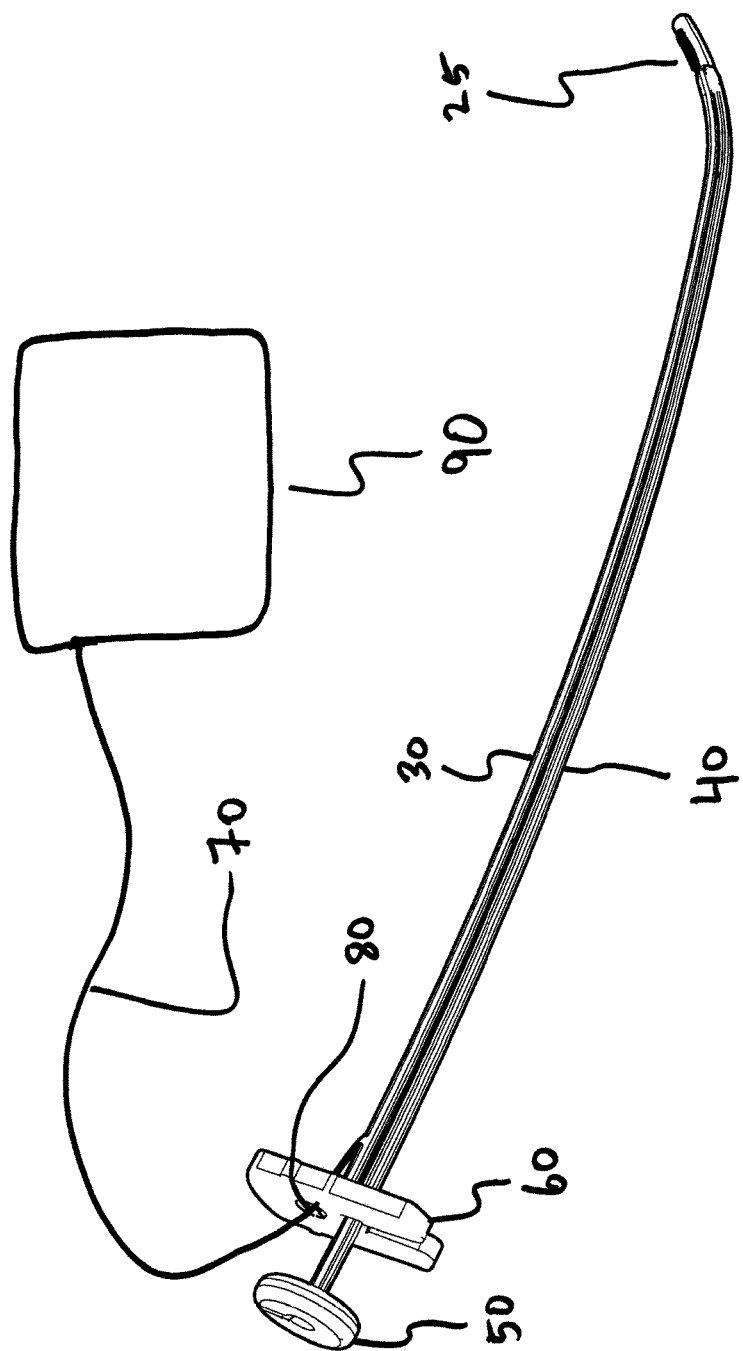
FIG. 5 is a perspective view of one embodiment of an imaging system of the disclosure.

With reference to FIGS. 4 and 5, the system may further include an image conduit (70) for transmission of electrical signals from the image acquisition element, to, for example, a display (90). As illustrated in FIGS. 4 and 5, image conduit (70) traverses the length of the second shaft (30) and through the second pressure receiving element (60) via hole (80) which traverses the thickness of the second pressure receiving element (60). Image conduit (70) allows electrical communication between the image acquisition element and, display (90) for example. As will be understood by those on the art, image conduit (70) may be coupled with multiple image acquisition elements for transmission of electrical signals. Further, while the embodiment shown FIGS. 4 and 5 depicts image conduit (70) as traversing the length of the second shaft (30), it will be understood that image conduit (70) may alternatively traverse the length of the first shaft (40). In various embodiments, the image conduit traverses the first or second shaft via a lumen or groove disposed within or on the surface of the respective shaft.

In addition to multiple image acquisition elements, the system of the disclosure may further include one or more illumination sources for illuminating the inside of a cavity to assist in image acquisition. For example, illuminating light may be provided to the interior of a cavity via an illumination source disposed along the stylet. In one embodiment, at least one illumination source is arranged on the stylet such that light is emitted distal to the distal tip of the stylet. The illumination source may be arranged in any manner that facilities illuminating the cavity. For instance, the illumination source may be arranged an array having a plurality of sources. One or more optical channels may be provided in the stylet to house the illumination source which may be equipped with its own power source or be in electrical communication with the display which may be equipped with functionality to operate the illumination source. In one embodiment, electrical communication for the illumination source may be achieved by integrating the wiring into the optical conduit. Alternatively, the illumination source may receive illuminating light from an external source or the display via an optical channel suitable to transmit light. The illumination source may emit any source of illumination including infrared, ultraviolet, visible light of one or more frequencies or white or colored light. Additionally, the illumination source may convey electromagnetic radiation of a specific nature (e.g., light of specific color or hue, laser light, infrared or ultraviolet light, and the like.). In one embodiment, the illumination source is employed to deliver electromagnetic radiation of a particular wavelength.

As an alternative to transmission of an acquired image through image conduit (70), an acquired image may also be wirelessly transferred to the display. As such, an image acquisition element of the disclosure may include functionality for wirelessly transmitting a signal, such as via a data communication link. Additionally, wireless communication pathways may be configured for secure, encrypted uni- or bi-directional data exchange. In particular, wireless functionality may include radio data communication, satellite data communication, Wi-Fi data communication, IrDA data communication, infrared data communication, Bluetooth™ data communication, and ZigBee™ data communication. Additional wireless communication protocols include, Wi-Fi™ 802.11a/b/g/n, Bluetooth®, or cellular data transfer protocols such as GSM, 3G. 4G, LTE and similar protocols for the wireless transfer of data.

As used herein, the term "display" refers to a device for providing a two-dimensional or three-dimensional representation of the image acquired by the image acquisition element. Commercially available versions of such displays include but are not liquid crystal displays as well as light emitting diodes (LED), polymer light emitting diodes (PLED), organic light emitting diodes (OLED), polymer organic light emitting diodes (PLOED), passive matrix organic light emitting diode (PMOLED), or active matrix organic light emitting diode (AMOLED) arrays. The use of OLED technology facilitates flexible displays and may be preferred where such flexible display technology is desirable. Multiple layers of transparent OLED layers may also be incorporated to provide three dimensional image display which may be useful in some applications where the apparatus of the present invention is used to visualize the use of remote manipulating tools where depth perception or three dimensional details are of interest to the operator. Such displays may also incorporate touch screen technology to facilitate manipulation (e.g. zoom, rotation, or perspective) of the image displayed on the display means.

In certain circumstances, it may be useful to have a power supply capable of supplementing the power supply of the system to facilitate extended use of the system and/or illumination source if so provided. It will be understood that the power source for the display of the disclosure may be external voltage from, for example, a wall outlet, or may be provided via batteries. Additionally, the amount of power supplied will be sufficient to also power all other components of the system, for example the image acquisition element as well as illumination sources if utilized. As used herein, batteries may be non-rechargeable or rechargeable. Examples of batteries useful in the practice of the present invention include zinc-carbon, zinc-chloride, alkaline (e.g., zinc-manganese dioxide), lithium (e.g., lithium-copper oxide, lithium-iron disulfide, lithium manganese dioxide), silver oxide, silver-zinc, NiCd, NiMH, NiZn, lithium ion batteries. The term battery includes a single cell or a plurality of two or more cells. For purposes of shipment and extended shelf life, there should be an operator removable physical barrier introduced between the power source and the circuitry of the remainder of the transmission module to preserve the power source during storage and shipment and guard against parasitic drain of power supply. When rechargeable batteries are used as the power source, the device of the present invention may also be provided with a recharging system adapted for the particular configuration and specifications of the rechargeable battery employed.

In various embodiments, images generated by the image acquisition element may be transferred to the display, and alternatively to a one or more additional displays. This may be accomplished by direct wireless transmission from the image acquisition element to the additional display or by wireless transmission from the primary display to the additional display. As such, the system provides for remote monitoring. For example, a supervising physician may be able to receive images acquired by different systems being utilized in multiple different rooms.

As shown in FIGS. 1-5, the first and second shaft of the stylet are coupled at the distal end of the stylet, with the first and second shafts being independent at the proximal end of the stylet. It will be understood that the point at which the first and second shaft are uncoupled to one another along the length of the stylet determines the amount of deflection of the distal tip as well as the size and location of the deflection zone. As such, the first and second shaft may be uncoupled at any point along the length of the stylet, for example the shafts are uncoupled at about 0.25, 0.50, 0.75, 1.0, 1.25, 1.50, 1.75, 2.0, 2.25, 2.50, 2.75, 3.0, 3.25, 3.50, 3.75, 4.0, 4.25, 4.50, 4.75, 5.0, 5.25, 5.50, 5.75, 6.0, 6.25, 6.50, 6.75, or 7.0 inches from the distal tip of the stylet. Further, the stylet may be configured to split into more than two independent shafts upon transition of the stylet to the deflected state. For example, each shaft may form 2, 3, 4, or 5 more independent shafts each connected to one another at various locations along the length of the stylet.

Additionally, while the embodiment shown in FIGS. 1-5 depicts the first and second shafts as being adjacent one another (i.e., side-by-side), it will be understood that the first and second shaft may be configured to be coextensive in a variety of geometries. For example, the one shaft may be disposed within a lumen or recess of the other along a portion of, or the entire length of the shafts. Additionally, it will be understood that the shafts may be manufactured of the same or different materials. For example one shaft may be more rigid than the other. In an embodiment, one shaft is disposed within a lumen or recess of the other along a portion of, or the entire length of the shafts, and one shaft is composed of material having a different elasticity than the other.

Any number of materials may be utilized in various components of the invention. Examples of suitable materials are well known in the art including thermoform or thermoset plastics but are not limited to polycarbonate (PC), polyethylene (PE), high density polyethylene (HDPE), polyetherimide (PEI), polysulfone (PSO), polyethersulfone (PES), polyethylene terepthalate (PET), polypropylene, polystyrene, high impact polystyrene (HIPS), acrylanitrile butadiene styrene (ABS), polyvinylchloride (PVC), acetal, Nylons (e.g., Nylon 4-6, Nylone 6-6, Nylon 11, or Nylon 12), acrylic-styreneacetonitrile (ASA), polyester liquid crystal polymer (LCP), stylene acrylonitrile (SAN), polyvinyldiene difluoride (PVDF), melamine, phenolics and the like. Typical procedures for forming the materials into suitable housing may be formed by compression molding, blow molding, casting, extrusion, pressure forming, and the like.

In one embodiment of the invention, one or more of the components of the present invention is/are fabricated from or coated with materials that provide improved non-slip surfaces, particularly when wet such as rubber, Neoprene or other suitable thermoplastic elastomers.

The present invention also provides software application capable of execution on elements of the system which are provided with microprocessors. For example, an application which upon initiation places the system in condition for display of the image conducted to the display from the Image acquisition device. For example such software would place the system in video mode, and optionally turn on the illumination source, and enable controls such as illumination level, zoom control, and focus control of the image acquisition device, recording, and broadcast of the signal to remote devices such as other networked computers and portable computing and communication devices such as smartphones.

The various steps in these functional processes or blocks that may be implemented in a variety of ways. It should also be noted that the various functions disclosed herein may be described using any number of combinations of hardware, firmware, and/or as data and/or instructions embodied in various machine-readable or computer-readable media, in terms of their behavioral, register transfer, logic component, and/or other characteristics. For example, the functions of various blocks can be combined with one another into any other number of modules.

Each module can be implemented as a software program stored on computer readable media provided in a component of the system. Computer-readable media in which such formatted data and/or instructions may be embodied include, but are not limited to, a tangible memory (e.g., random access memory, read only memory, etc.) to be read by a central processing unit to implement the functions.

The application software may be accessed from within or loaded into a component of the system. As disclosed herein, embodiments and features of the invention may be implemented through computer-hardware, software and/or firmware. Although some of the disclosed implementations describe components such as software, systems and methods consistent with the innovations herein may be implemented with any combination of hardware, software and/or firmware.

Figure 2:
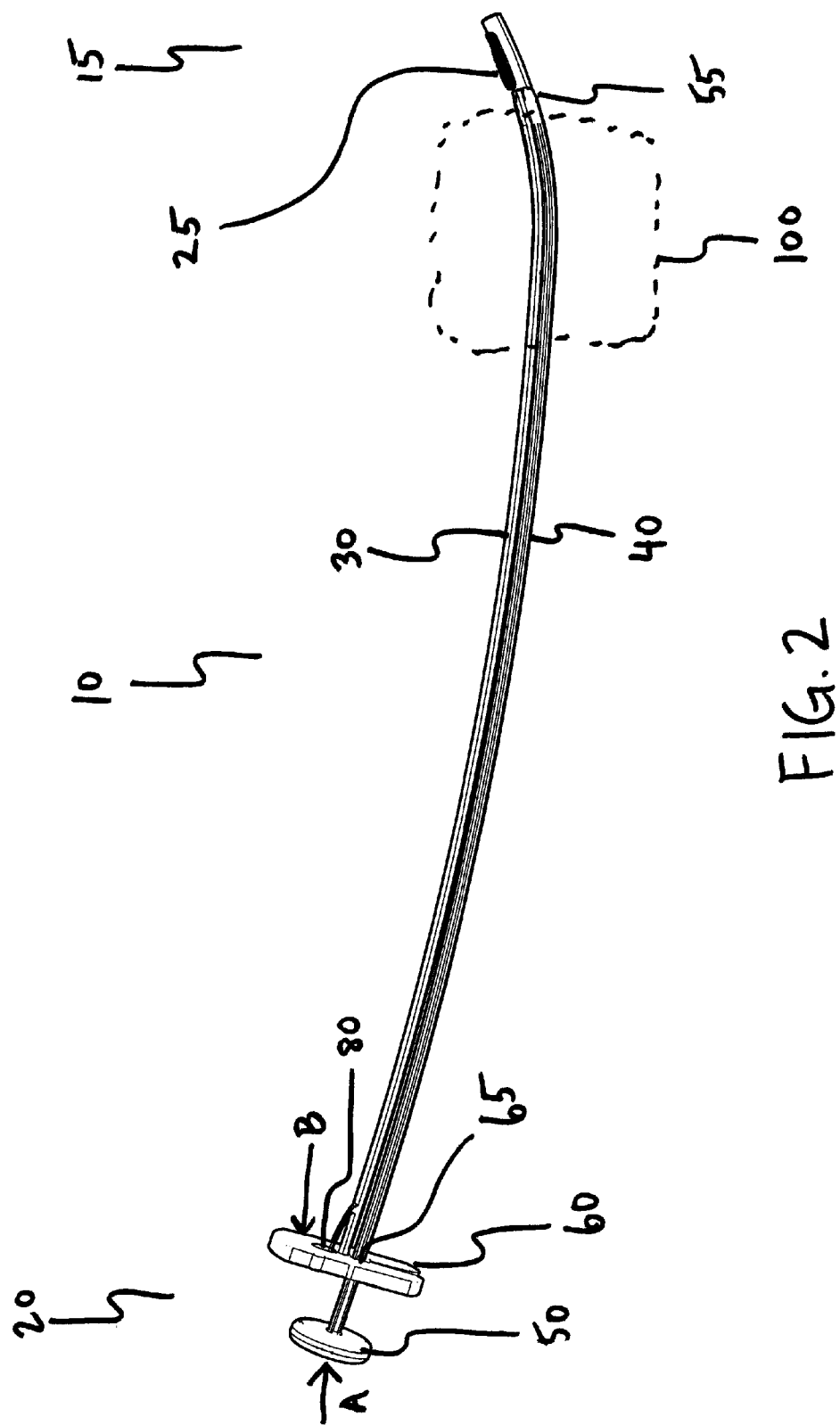
FIG. 2 is a side view of one embodiment of a stylet of the disclosure.
Figure 3:
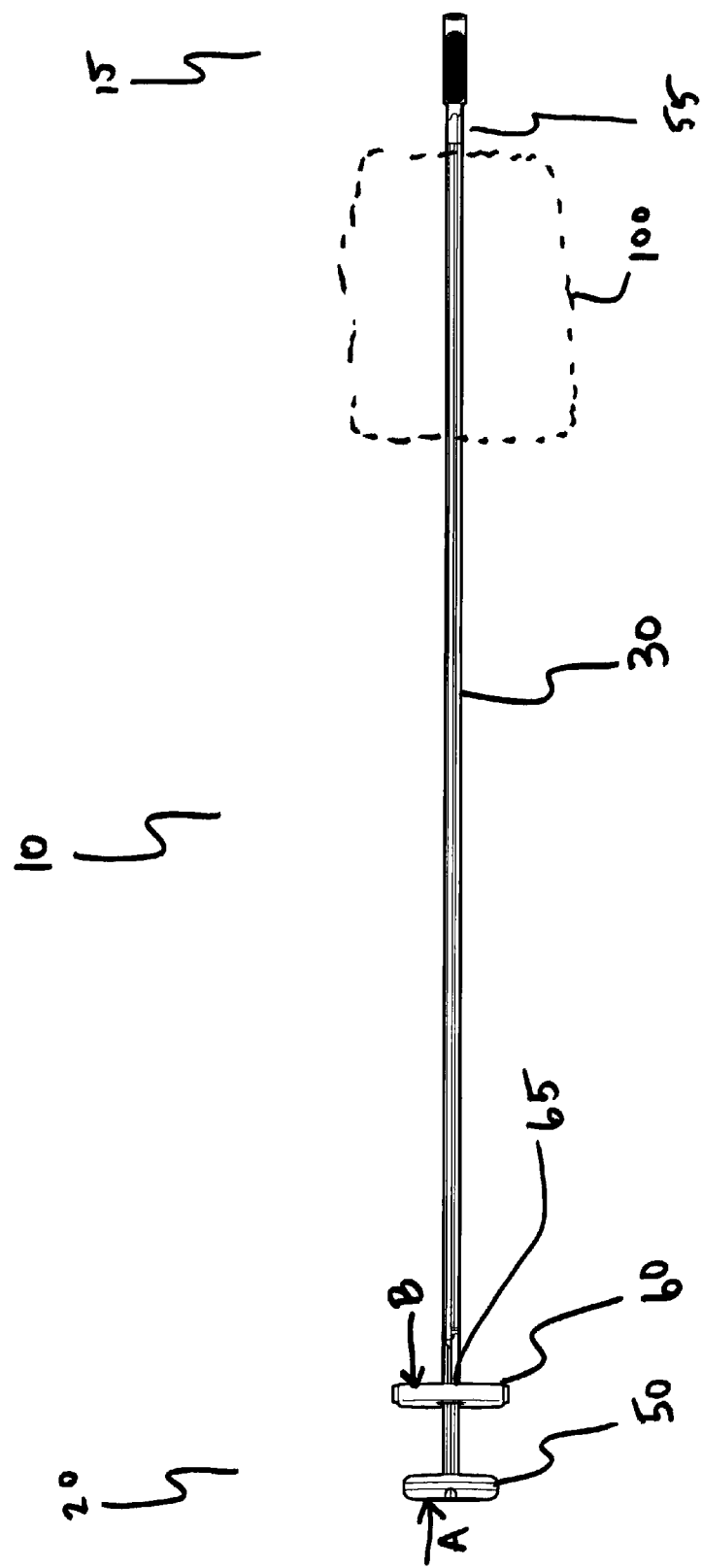
FIG. 3 is a top view of one embodiment of a stylet of the disclosure.

The system of the present disclosure may further include a malleable rod (35). The rod may be received within a lumen or groove which traverses all or a portion of the length of the stylet. Again with reference to FIGS. 1-3, in one embodiment, first shaft (40) includes a central lumen or recess traversing all or a portion of its length, and accessed by opening (85) in the first pressure receiving element (50). While the embodiment of FIGS. 1-3 depicts the first shaft being configured to receive the malleable rod (35), it will be understood that the second shaft may alternatively, or also, be configured to receive the malleable rod (35). The malleable rod (35) is inserted into the shaft such that the shaft may be bent to have a predetermined shape or deflection. In various embodiments, the first or second pressure receiving element is provided with a recess configured to house the end of the malleable rod (35) so that the end of the rod (35) does not interfere with the user. For example, the embodiment shown in FIG. 1 includes recess (95) in the first pressure receiving element (50).

The display allows the user to view the inside of a cavity while manipulating the distal end of the stylet within the cavity. This is extremely advantageous when conducting medical procedures such as endotracheal intubation of a subject which requires exact placement and advancement of the distal tip of the stylet into the trachea. Ideally, the display is positioned such that the user may easily view the display while also manipulating and operating the stylet. In one embodiment, the display is adapted to be worn on the wrist of a user so that the user has a direct view of the display at all times during an intubation procedure. For example, the display may be attached to a sleeve to be worn by the user. Alternatively, the system may also include a display holder to house the display having a malleable or articulating arm adapted to attach or couple to an object in the user's surrounding, such as an IV pole, side rail or operating room table.

As discussed herein, the stylet of the disclosure transitions from a first relaxed configuration to a second deflected state upon application of opposing forces to the first and second pressure receiving elements. As shown in FIGS. 1-3, application of opposing forces (arrows A and B) to the first and second pressure receiving elements (50, 60) produces a deflection in the deflectable section (100). As such, application of opposing forces allows deflection of the tip to be adjusted while entering a confined space, such as an airway. Typically, the stylet is transitioned from the first configuration to the second configuration by forces applied by a thumb and one or more fingers of a user such that the first and second pressure receiving elements are squeezed together. However, it will be appreciated by those in the art that such a force may be generated in a variety of ways. For example, in one embodiment, the first and second pressure receiving elements of the stylet may by electromechanically coupled and configured to draw the first and second pressure receiving elements closer to one another. The stylet may further include an actuator to facilitate generation of force. In various embodiments, the electromechanical coupling may be voice activated or activated by a mechanical or digital switch.

Additionally, the system of the disclosure may be configured such that the stylet may be maintained in a particular configuration, for example, the first relaxed configuration or the second deflected configuration. One in the art would appreciate that this may be accomplished in a variety of ways. In one embodiment, the stylet may be configured such that the first and second pressure receiving elements interlock with one another during transitioning of the stylet between configurations. This may be achieved via the electromagnetic coupling or alternatively, the first and second pressure receiving elements may include releasably interlocking elements that prevent transition of the stylet back to the relaxed configuration while the stylet is being deflected.

Figure 6:
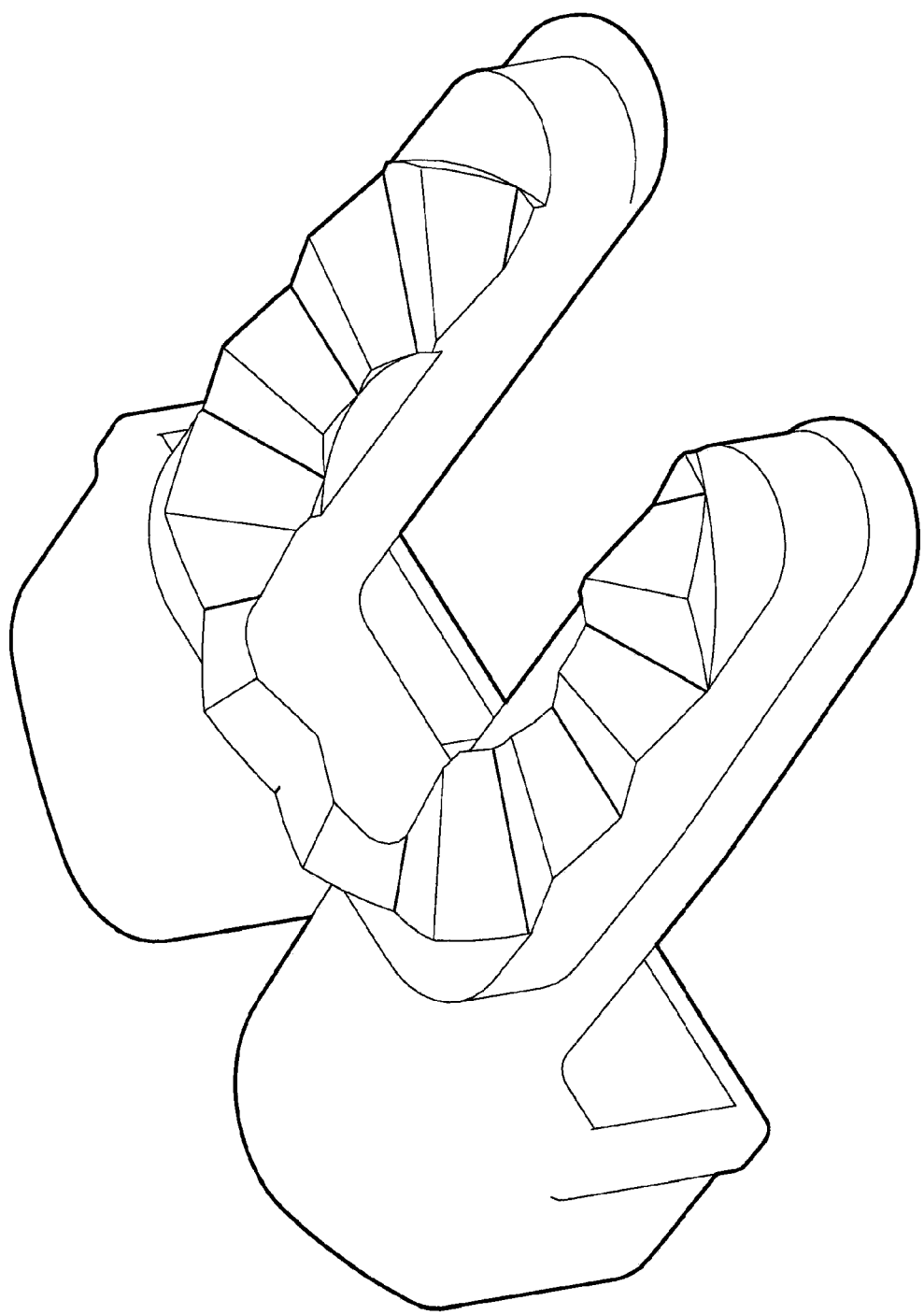
FIG. 6 is a perspective view of one embodiment of a spacer of the disclosure.
Figure 7:
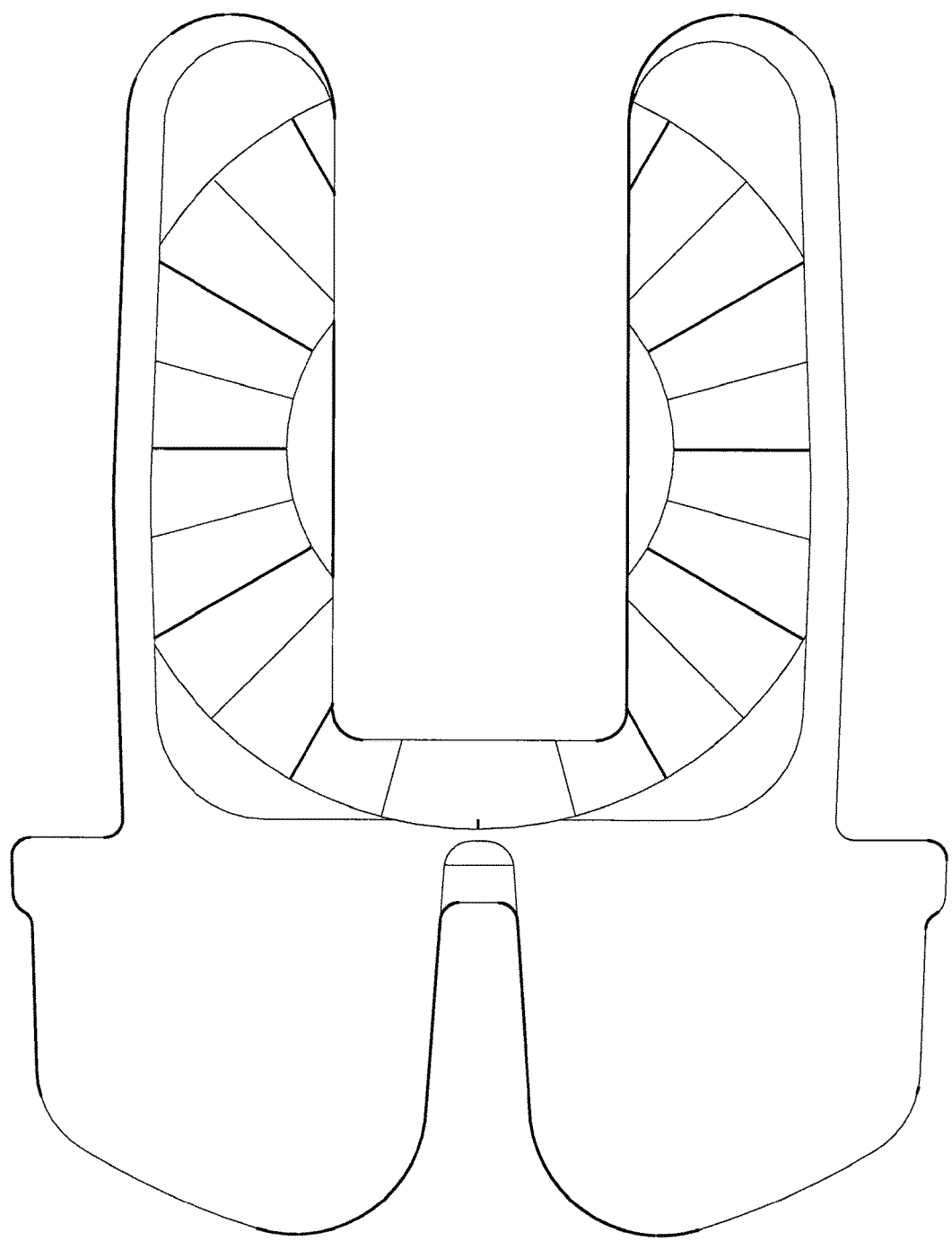
FIG. 7 is a front view of one embodiment of a spacer of the disclosure.
Figure 8:
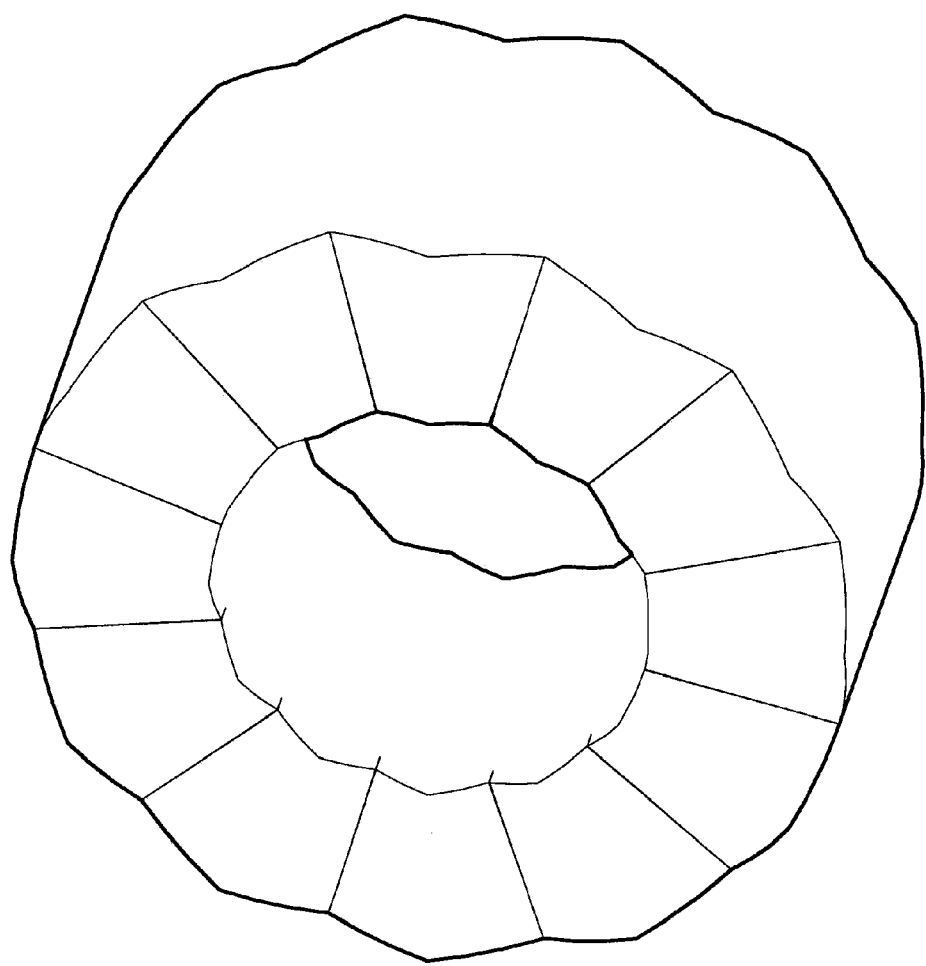
FIG. 8 is a perspective view of one embodiment of a spacer of the disclosure.
Figure 9:
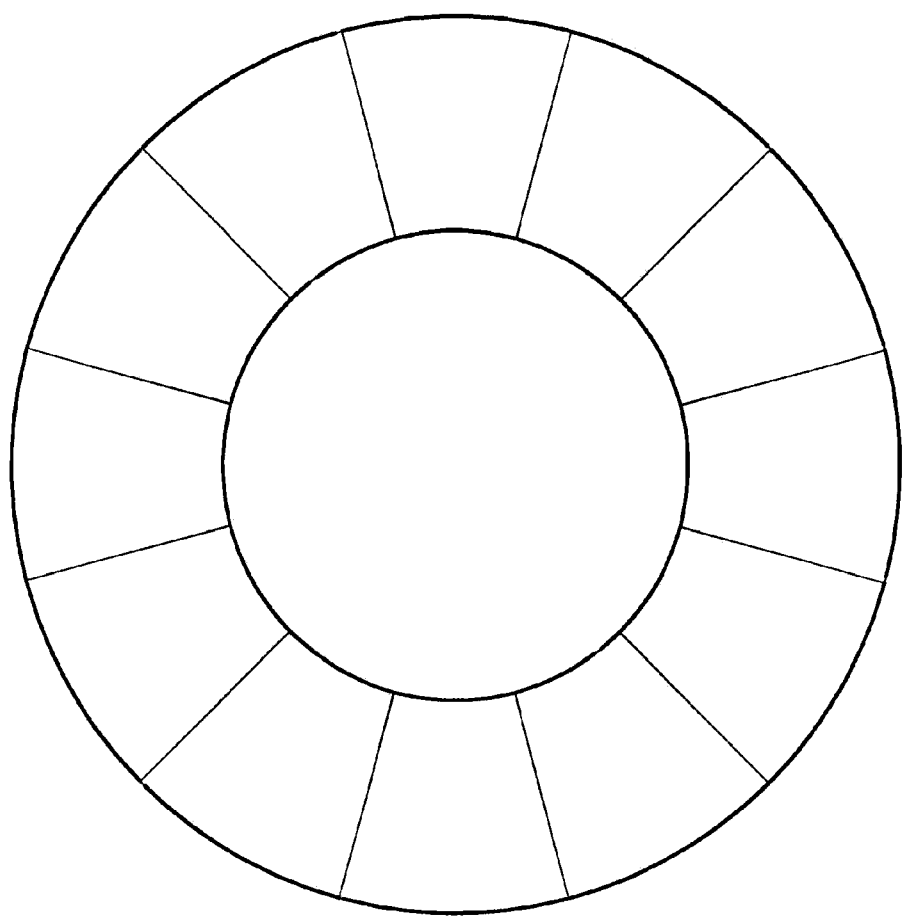
FIG. 9 is a front view of one embodiment of a spacer of the disclosure.
Figure 10:
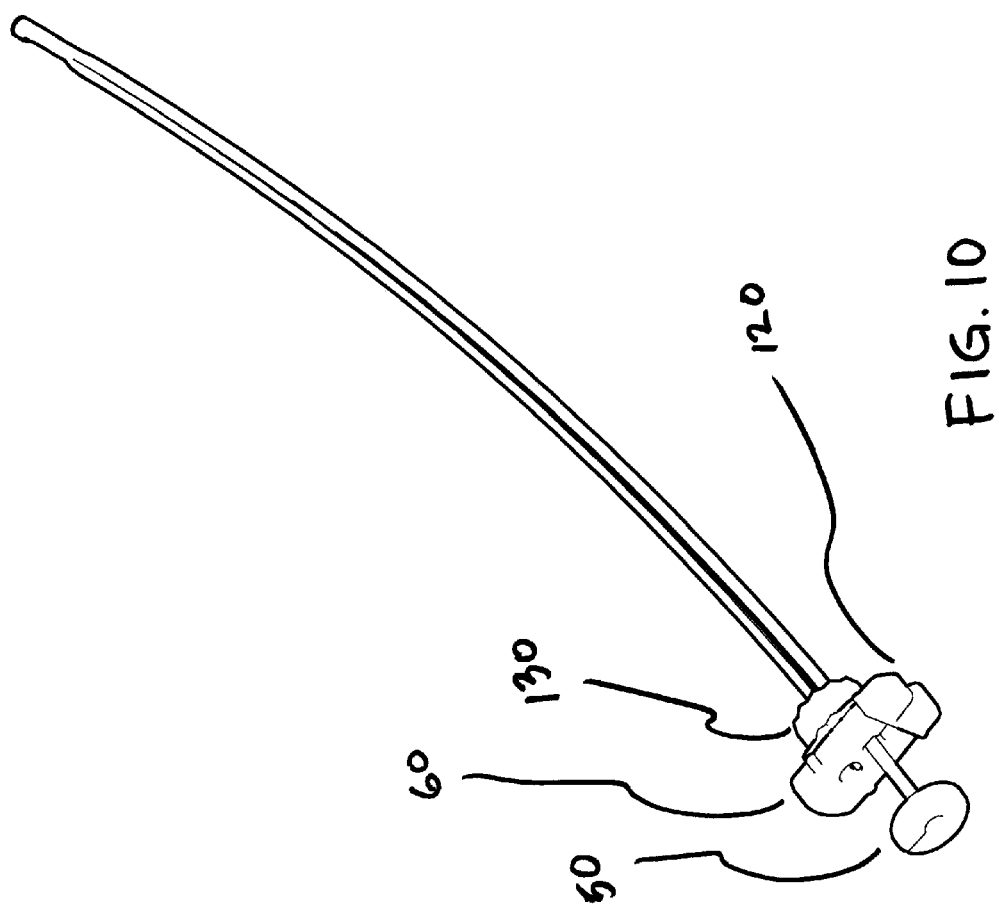
FIG. 10 is a perspective view of one embodiment of a stylet of the disclosure with spacers.
Figure 11:
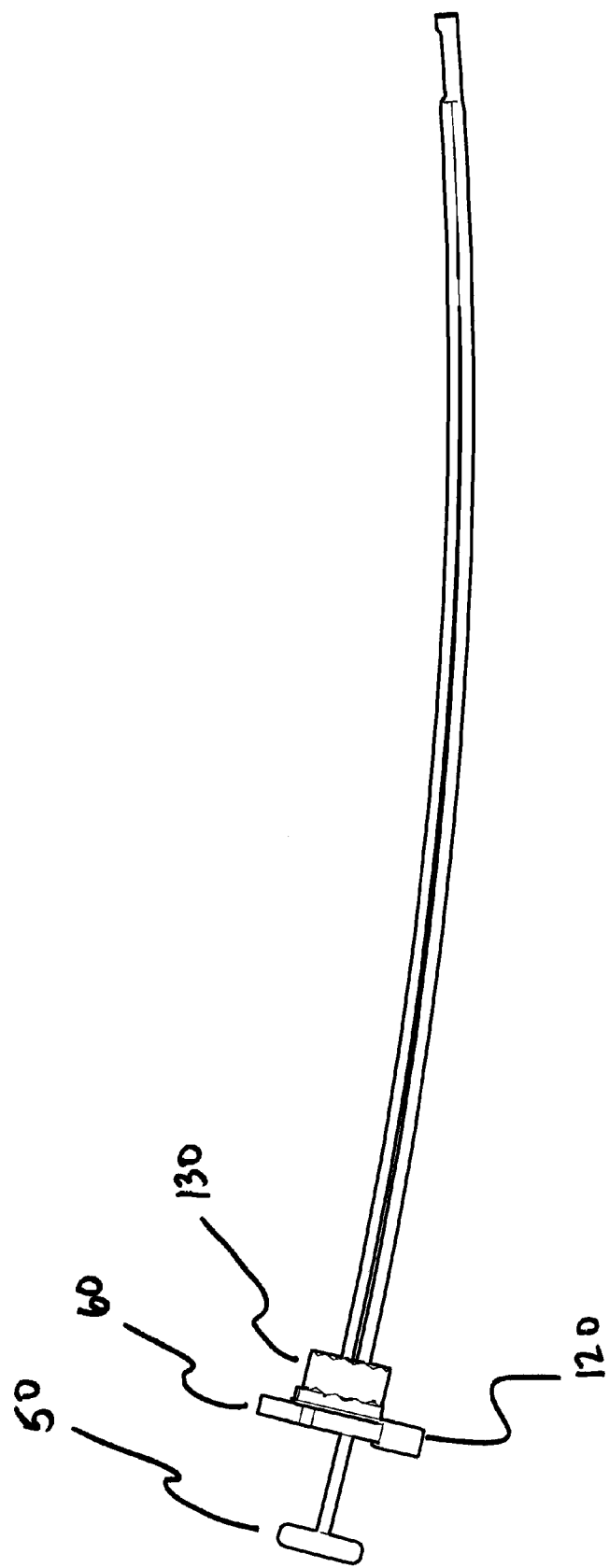
FIG. 11 is a side view of one embodiment of a spacer of the disclosure with spacers.
Figure 12:
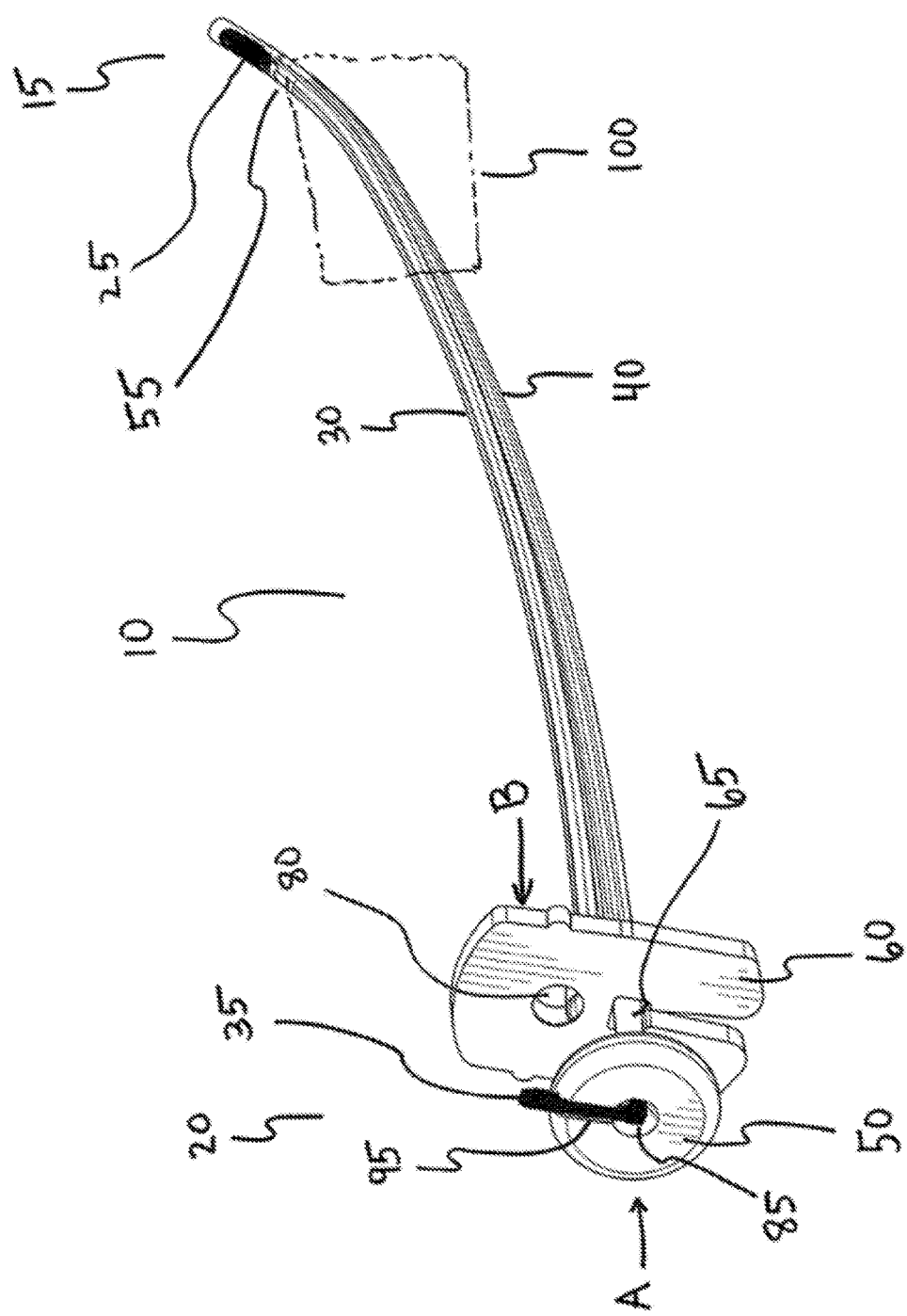
FIG. 12 is a perspective view of the stylet of FIG. 1 having a malleable rod (35) disposed in the first shaft (40) via opening (85).

Advantageously, the stylet of the system of the disclosure, is adaptable to be used with accessory devices of different lengths and types. For example, the length of the stylet may be altered by inclusion of spacers that may be disposed over that first and second shafts of the stylet. FIGS. 6-9 illustrate spacers that may be utilized with the present system embodiments of the invention. FIGS. 6 and 7 depict an embodiment of a spacer that is disposed over the stylet shaft and configured to couple to a pressure receiving element. FIGS. 8 and 9 illustrate an embodiment of a spacer that is disposed over the stylet shaft and configured to engage the spacer shown in FIGS. 6 and 7. As shown in FIGS. 10 and 11, spacer (120; that shown in FIGS. 6 and 7) couples with the second pressure receiving element (60) and engages a second spacer (130; that shown in FIGS. 9 and 10). The spacers may be configured or shaped such that rotational motion between the spacers is prevented. This may be accomplished in a number of ways. For example, the spacers may include surface grooves or ridges that prevent rotation with an adjacent spacer. In various embodiments, a stylet may be configured to include any number of spacers, such as 1, 2, 3, 4, 5, 6, 7, 8 or more spacers.

The ability to adjust the length of the stylet allows the system to be used with a variety of accessory devices of different lengths and types. For example, the system of the disclosure is adaptable for use with accessory devices for both pediatric and adult application, such as pediatric and adult endotracheal tubes.

The system of the disclosure is ideal for use with a video laryngoscope, video supraglottic airway, video endotracheal tube or a video oral airway. In addition to its use as a device capable of delivering immediate visual verification of correct endotracheal tube placement (faster and more accurate than either the capnography or breath sounds), this system has the added benefit of being a standalone low-cost alternative to video laryngoscopes for use with difficult intubations. It can also augment the use of a video laryngoscope by providing a view of the larynx from the tip of the endotracheal tube during intubation thus providing an immediate image of a correctly placed (trachea) or incorrectly placed (esophagus) endotracheal tube. The view of the larynx is often obstructed during video laryngoscope intubation as the distal end of the endotracheal tube passes in front of the video laryngoscope's camera. Additionally, the correct endotracheal tube depth placement within the trachea can be quickly visually verified thus preventing an inadvertent endobronchial intubation; a benefit not provided by a video laryngoscope used without this invention.

In one aspect, the system of the disclosure is used for intubating a subject. As such the invention provides a method for intubating a subject. Generally, the method includes inserting the stylet of the disclosure into an endotracheal tube. The stylet and the endotracheal tube are then inserted into the airway of the subject. The airway of the subject is visualized via images acquired by the image acquisition element and transmitted to the display. The stylet and the endotracheal tube are then inserted into the trachea of the subject and subsequently the stylet is removed from the subject's trachea. In embodiments, the method may further include confirming correct depth of placement of the endotracheal tube in the trachea of the subject. Additionally, a malleable rod may be inserted into the first or second shaft of the stylet and bent to a desired curvature before inserting the stylet into the airway.

The ability to controllably place a display near the patient's oral opening allows the laryngoscopist to intubate the patient without having to move his head and neck to view a distant screen. A display placed near or adjacent to the proximal end of a stylet or endotracheal tube is similarly out of the laryngoscopist's field of view during direct laryngoscopy. Any small movement of the head and neck away from the view during direct laryngoscopy complicates visualization of the vocal cords and can lead to injury of the teeth, gums, or lips.

This allows the laryngoscopist to view the larynx with direct vision by using standard laryngoscope blades such as the Miller blade and MAC blade without changing technique. Because of their low profile and non-accentuated curvature when compared to video laryngoscopic blades, they are typically preferred by experienced laryngoscopists. Thus, the laryngoscopist needs only to move his eyes to rapidly switch between direct and video views of the larynx. Direct laryngoscopy is thus augmented with a system that does not require a significant 'learning curve' to use successfully.

As used herein, the term "patient" or "subject" refers to a variety of animal types. Generally the patient or subject is human, although as will be appreciated by those in the art, the patient or subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition. As such, it is clear that the system of the invention may be utilized in veterinary applications.

The present invention is useful in the visualization of any space, particularly confined spaces not amenable to direct visualization. Therefore, the present invention is useful in a variety of fields including but not limited to medical treatment and diagnosis, surveillance including law enforcement and military applications, inspection of machinery without disassembly and automotive applications. As such, the invention provides a method of imaging a confined space. The method includes inserting a stylet or device of the disclosure into the confined space, and visualizing the space via an image acquisition element before, during or after insertion of the device into the confined space, thereby imaging the confined space.

The present invention is useful for surveillance, particularly in the fields of law enforcement or military applications. For example, the image conduit may be threaded through very small spaces to enable visualization of the interiors of rooms or confuted spaces while minimizing the exposure of the operator to potentially dangerous situations. For example, the present invention may be used to visualize spaces which may contain explosive devices or contraband. Commercially available image sensors are capable of recognizing light outside the visible spectrum or in low or zero lux conditions. Consequently, the present invention may be useful as a "night vision" surveillance system to enable the operator to obtain an image of a space in the substantial absence of ambient light. As previously discussed, the illumination source of the present invention may provide illumination in a frequency range outside the visible spectrum and such non-visible light sources may be employed to invisibly illuminate an area and enhance such "night vision" capabilities.

The present invention is also useful in a variety of automotive applications. For example, the image conduit may be threaded through small spaces such as spark plug holes to enable visualization of the interiors of cylinders, intake and/or exhaust valves, intake and exhaust systems, HVAC systems, to inspect the status and operation of enclosed mechanical mechanisms without disassembly (e.g., window mechanisms, door locking mechanisms, transmissions, differentials, fuel systems, and the like), assess the state of replaceable parts such as brake linings or clutches, and the like.

In another aspect, the invention provides a kit. The kit may include an imaging system or intubation device as described herein. The kit may further include instructions for obtaining images of a confined space, such as an airway. In some embodiments, the kit further includes one or more spacer elements, an endotracheal tube, a malleable rod, a display, or a combination thereof.

Although the invention has been described with reference to the above example, it will be understood that modifications and variations are encompassed within the spirit and scope of the invention. Accordingly, the invention is limited only by the following claims.

What is claimed is:

1. An intubation device comprising:
    a) a distally deflectable and proximally flexible stylet having a distal end, a proximal end and a deflectable section disposed therebetween and proximate to the distal end, the stylet further comprising:
        i) a first flexible shaft having a distal end and a proximal end; and
        ii) a second flexible shaft having a distal end and a proximal end, the distal end of the second flexible shaft being coupled to the distal end of the first flexible shaft at the distal end of the stylet, wherein application of opposing forces to the first and second flexible shafts produces angular deflection in the deflectable section; and
    b) a malleable rod stylet removably disposed within a lumen of the distally deflectable and proximally flexible stylet and extending along the length of the first or second flexible shaft, wherein the rod is configured such that it is capable of having a predetermined bend to facilitate insertion to a larynx, and is removable to facilitate insertion into a trachea.

2. The intubation device of claim 1, further comprising an illumination source disposed toward the distal end of the stylet.

3. The intubation device of claim 2, wherein the illumination source is arranged as an array.

4. The intubation device of claim 1, wherein the first and second shafts are operable to reversibly couple at the proximal end of each shaft when the opposing forces are applied.

5. The intubation device of claim 1, wherein the first and second shafts are operable to couple to retain the stylet in a deflected state when the opposing forces are removed.

6. The intubation device of claim 5, wherein the first and second shafts interlock via pressure receiving elements.

7. The intubation device of claim 1, further comprising an actuator configured to apply pressure to the first and second shafts.

8. The intubation device of claim 7, wherein the actuator is voice activated.

9. The intubation device of claim 1, wherein the device is adapted for single use.

10. The intubation device of claim 1, further comprising an endotracheal tube.

11. The intubation device of claim 1, further comprising an image acquisition element disposed toward the distal end of the stylet.

12. The intubation device of claim 11, further comprising a display in electronic communication with the image acquisition element.

13. The intubation device of claim 12, wherein the display is in wireless communication with the image acquisition element.

* * * * *